United States Patent
Lai

(10) Patent No.: US 7,363,944 B2
(45) Date of Patent: Apr. 29, 2008

(54) SEALING MECHANISM FOR DIAPHRAGM TANK

(76) Inventor: Han-Chin Lai, No. 238, Sec 1 Shen-Lin Road, Taya Hsing, Taiching (TW)

( * ) Notice: Subject to any disclaimer, the term of this patent is extended or adjusted under 35 U.S.C. 154(b) by 0 days.

(21) Appl. No.: 11/006,402

(22) Filed: Dec. 6, 2004

(65) Prior Publication Data
US 2005/0194389 A1    Sep. 8, 2005

Related U.S. Application Data

(63) Continuation of application No. 10/773,985, filed on Feb. 6, 2004, now abandoned.

(51) Int. Cl.
*F16L 55/04* (2006.01)
(52) U.S. Cl. .............. 138/30; 138/26; 220/720; 220/723
(58) Field of Classification Search ............... 220/720, 220/721, 723, 601, 661, 4.12; 138/26, 30
See application file for complete search history.

(56) References Cited

U.S. PATENT DOCUMENTS

| | | | | |
|---|---|---|---|---|
| 2,343,440 A | | 3/1944 | Andrus ............... 204/196.15 |
| 2,877,801 A | * | 3/1959 | Mercier ............... 138/30 |
| 3,208,775 A | | 9/1965 | Stap et al. ............ 285/204 |
| 3,230,975 A | * | 1/1966 | Mercier ............... 138/30 |
| 3,232,318 A | * | 2/1966 | Mercier ............... 138/30 |
| 3,247,999 A | * | 4/1966 | Stilwell ............... 383/127 |
| 3,524,475 A | * | 8/1970 | Kirk, Jr. ............... 138/30 |
| 4,765,507 A | * | 8/1988 | Yavorsky et al. ...... 220/590 |
| 5,222,620 A | * | 6/1993 | Lima et al. ............ 220/495.08 |
| 5,379,913 A | * | 1/1995 | Rieke et al. .......... 220/601 |
| 5,551,590 A | * | 9/1996 | Mazur et al. .......... 220/23.83 |
| 6,264,247 B1 | * | 7/2001 | Lombari et al. ........ 285/202 |
| 6,517,117 B1 | | 2/2003 | Lai ..................... 285/202 |
| 6,915,922 B2 | * | 7/2005 | Wang ................... 220/720 |
| 7,303,091 B2 | * | 12/2007 | Lombari ............... 220/721 |
| 2004/0173624 A1 | * | 9/2004 | Carter ................. 220/720 |
| 2005/0017016 A1 | * | 1/2005 | Lombari ............... 220/721 |

* cited by examiner

*Primary Examiner*—James Hook
(74) *Attorney, Agent, or Firm*—Choate, Hall & Stewart LLP

(57) ABSTRACT

A liner for use with a diaphragm tank and a through-wall connector. The through-wall connector includes a passage fitting having a neck and adapted to extend into the diaphragm tank, an o-ring mounted on the passage fitting, and an annular holder mounted on the passage fitting and having an annular groove. The liner has a raised portion defining an annular groove to receive the o-ring.

3 Claims, 3 Drawing Sheets ated Feb. 6, 2004 now abandoned, the entire contents of which are incorporated by reference herein.

SEALING MECHANISM FOR DIAPHRAGM TANK

This application is a continuation of and claims the priority of U.S. patent application Ser. No. 10/773,985, filed Feb. 6, 2004 now abandoned, the entire contents of which are incorporated by reference herein.

FIELD OF THE INVENTION

This invention pertains to improvements for diaphragm expansion tanks, and, more particularly, to a mechanism to better seal the bladder of an expansion tank.

BACKGROUND OF THE INVENTION

A diaphragm tank 12 for potable water typically has a metal shell 22 and a plastic liner 24 (FIG. 1). A diaphragm 26 is mounted below the liner 24, defining an air cushion between the shell 22 and the diaphragm 26 and an expandable bladder enclosed by diaphragm 26 and liner 24. A gasket 28 is usually mounted around the hole between the shell 22 and the liner 24 to stiffen the metal shell 22 and plastic liner 24 in the area of the hole and to form an airtight seal to block the leakage of air (FIG. 2).

A connector 10 is mounted on diaphragm tank 12 to allow fluid to flow into or out of the tank (FIG. 1). Connector 10 extends through both the shell 22 and the liner 24. A conventional connector includes a passage fitting 14 and an o-ring 16 mounted around the passage fitting 14 (FIG. 2). The interior end of the passage fitting 14 is bent into a curled end 18 to retain the o-ring 16 on the passage fitting 14. A shoulder 20 abuts the outside of the tank 12, allowing the wall of tank 12 to be clamped between the shoulder 20 and the curled end 18 of the passage fitting 14.

The connector 10 links the tank to a water flow. When the pressure of the flowing water is greater than that of the air cushion, water flows into the bladder. When the water pressure decreases, the pressurized air in the tank expands against the bladder, pushing the water out until the air pressure is the same as the water pressure or the tank is empty.

As shown in FIG. 2, a large force is required to press the curled end 18 around o-ring 16, and curled end 18 will easily be cracked. This reduces the pressure on o-ring 16, reducing its ability to seal the connector 10 and reducing the strength of the passage fitting 14. In addition, the diameter of the contact area between the curled end 18 of the passage fitting 14 and the liner 24 is only slightly larger than the diameter of the hole, allowing a gap to form between liner 24 and gasket 28. This allows air from the tank 12 to enter the water resident in the space between liner 24 and diaphragm 26. Because the air in the tank does not circulate, it may contain harmful bacteria and other microorganisms that could cause disease if air retained in the tank was allowed to mix with the water passing in and out of the bladder. As a result, it is desirable to have a more robust seal between the connector and the remainder of the tank.

SUMMARY OF THE INVENTION

In one aspect, the invention is a diaphragm tank. The tank comprises an outer shell, a flexible diaphragm, a liner sealingly connected to the flexible diaphragm to define a bladder and including an orifice and a raised portion surrounding the orifice that defines an annular groove, a passage fitting providing fluidic communication between an exterior of the outer shell and the bladder and having a neck, an o-ring disposed in the annular groove, an annular holder mounted on the passage fitting and having a groove and a gasket disposed between the liner and the outer shell. The annular holder is adapted to rest on the raised portion and retain the o-ring within the annular groove, and a portion of the neck is bent to retain the holder against the o-ring, thereby preventing fluidic communication between a space between the liner and the outer shell and the bladder along an outer wall of the passage fitting. The passage fitting may be disposed partially inside the outer shell and partially outside the outer shell and comprise a shoulder adapted to restrict motion of the passage fitting into diaphragm tank.

In another aspect, the invention is a diaphragm tank. The diaphragm tank comprises an outer shell, a flexible diaphragm, a liner sealingly connected to the flexible diaphragm to define a bladder and including an orifice and a raised portion surrounding the orifice that defines a relief surface, a passage fitting providing fluidic communication between an exterior of the outer shell and the bladder and having a neck, an o-ring disposed on the relief surface, an annular holder mounted on the passage fitting and having a groove, and a gasket disposed between the liner and the outer shell. The annular holder is adapted to retain the o-ring on the relief surface, and a portion of the neck is bent to retain the holder against the o-ring, thereby preventing fluidic communication between a space between the liner and the outer shell and the bladder along an outer wall of the passage fitting.

In another aspect, the invention is a liner for use with a diaphragm tank and a through-wall connector, the through-wall connector comprising a passage fitting having a neck and adapted to extend into the diaphragm tank, an o-ring mounted on the passage fitting, an annular holder mounted on the passage fitting and having an annular groove, wherein the liner has a raised portion defining an annular groove to receive the o-ring, and, when the neck is bent over the holder, the annular groove on the holder fits around the raised portion and the o-ring, thereby preventing fluidic communication from an exterior side of the liner to an interior side of the liner along an outer surface of the passage fitting.

In another aspect, the invention is a liner for use with a diaphragm tank and a through-wall connector, the through-wall connector comprising a passage fitting having a neck and adapted to extend into the diaphragm tank, an o-ring mounted on the passage fitting, an annular holder mounted on the passage fitting and having an annular groove, wherein the liner has a raised portion having a relief surface on which the o-ring is disposed, and, when the neck is bent over the holder, the annular groove on the holder fits around the o-ring disposed on the relief surface of the passage fitting, thereby preventing fluidic communication from an exterior side of the liner to an interior side of the liner along an outer surface of the passage fitting.

BRIEF DESCRIPTION OF THE DRAWING

The invention is described with reference to the several figures of the drawing, in which.

DETAILED DESCRIPTION OF CERTAIN PREFERRED EMBODIMENTS

Figure 1:
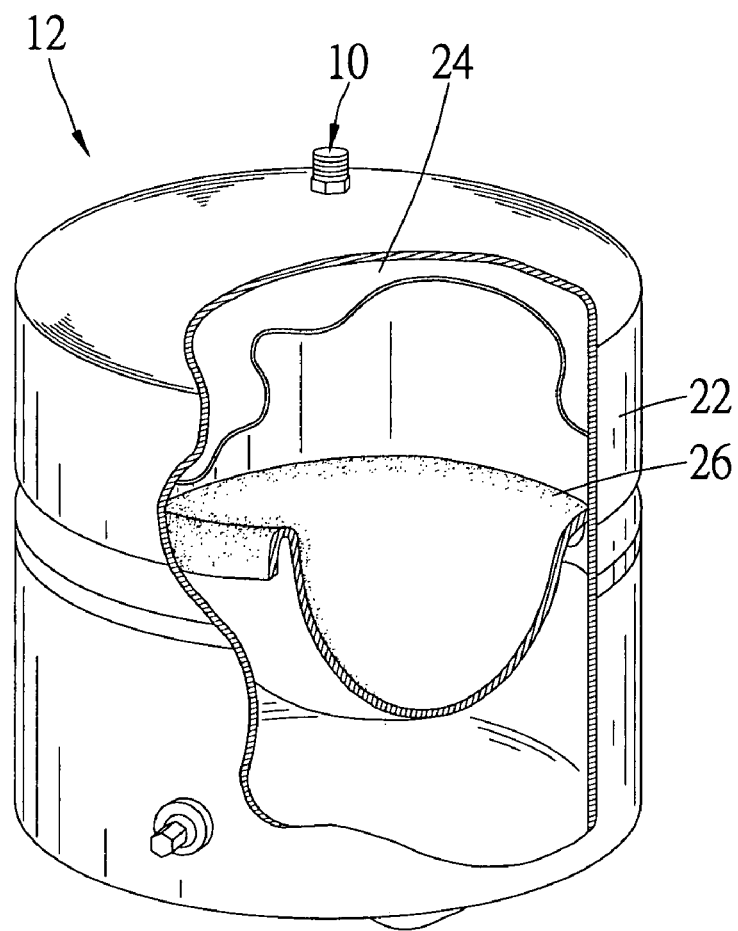
FIG. 1 is a perspective view of a diaphragm tank with a conventional connector.
Figure 2:
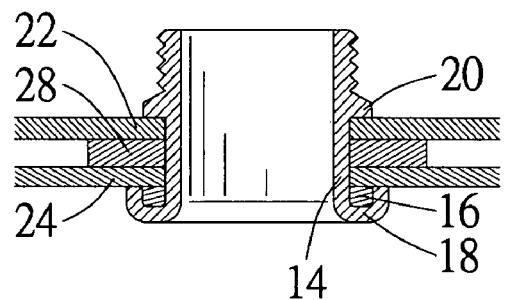
FIG. 2 is a cross-sectional view of the connector depicted in FIG. 1.
Figure 3A:
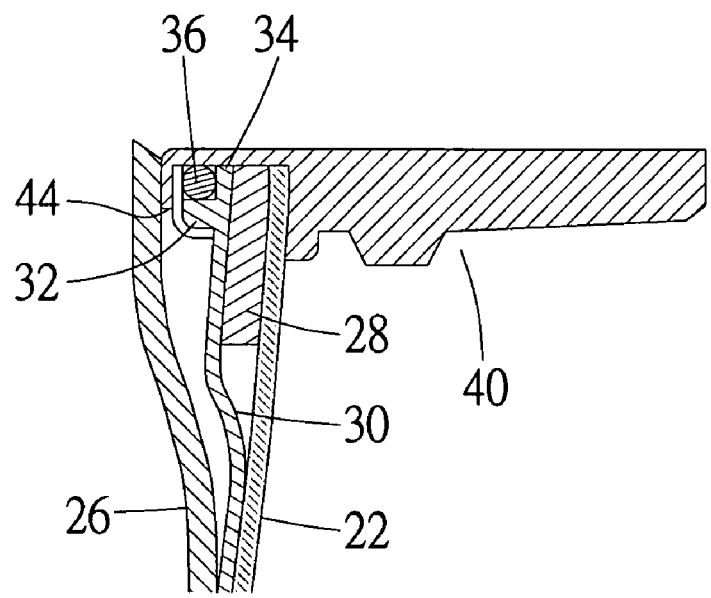
FIG. 3A is a partial cross-sectional view of a connector and tank according to an embodiment of the invention.
Figure 3B:
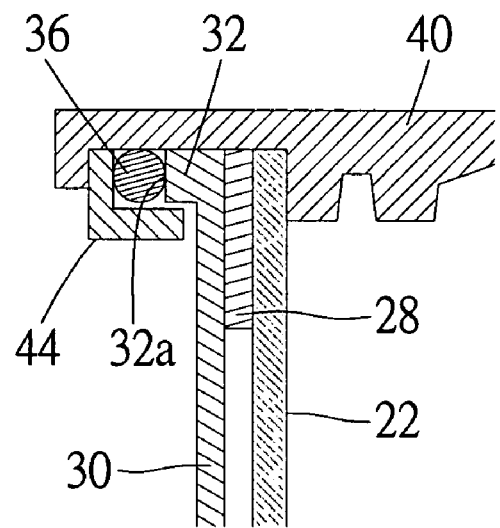
FIG. 3B is a partial cross-sectional view of a connector and tank according to an alternative embodiment of the invention from that depicted in FIG. 3A.

The invention includes a liner for a diaphragm tank. In one embodiment, the liner 30 rests inside the outer shell 22 of a diaphragm tank (FIG. 3A). The liner 30 includes a raised portion 32 that defines an annular groove 34. An o-ring 36 disposed in groove 34 provides a seal preventing fluidic communication between an expandable bladder defined by liner 30 and diaphragm 26 and the space between liner 30 and outer shell 22. In an alternative embodiment, groove 34 is omitted (FIG. 3B). Rather, raised portion 32 presents a relief surface 32a, e.g., a surface elevated with respect to the neighboring portion of liner 30, on which o-ring 36 rests. The raised portion 32 defines an annulus that accommodates passage fitting 40.

The construction of diaphragm tanks is well known to those skilled in the art. Liner 30 is easily fabricated by injection molding, although alternative manufacturing techniques may be used. Exemplary materials for liner 30 include polypropylene, teflon, nylon, polyalkylene terephthalate, polyformaldehyde, polystyrene, poly(methyl methacrylate), polycarbonate, and poly(hexylisocyanate).

Figure 4:
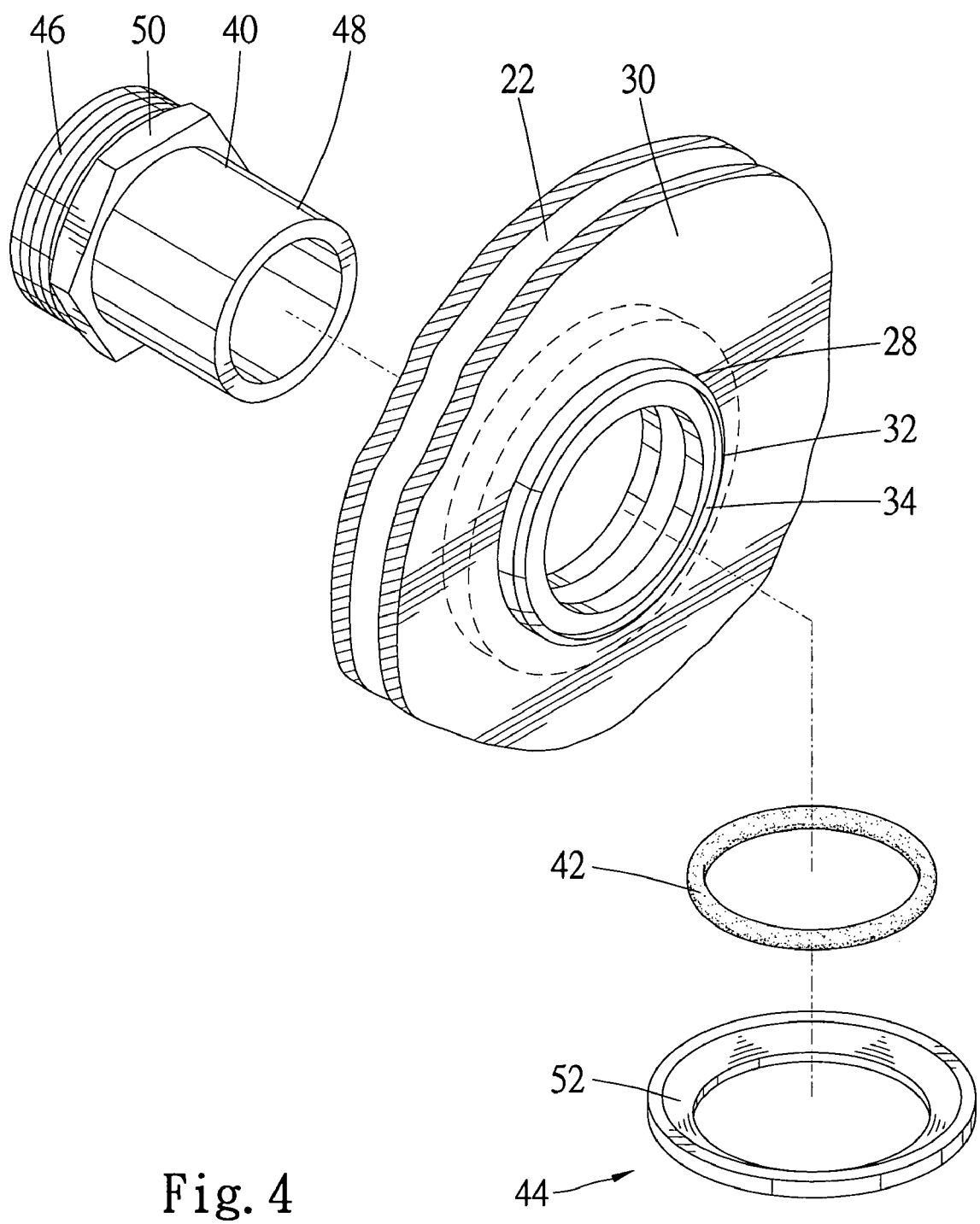
FIG. 4 is an exploded prospective view of a liner according to an embodiment of the invention and a connector for use therewith.

An exemplary connector for use with an embodiment of the present invention comprises a passage fitting 40, an o-ring 42 and an annular holder 44 (FIG. 4). The passage fitting 40 extends through the outer shell 22 and liner 30 of the diaphragm tank. Passage fitting 40 may include a thread 46 that extends out from the tank to connect with a hose, pipe or other plumbing. One skilled in the art will recognize that the thread may also be tapped on the interior of passage fitting 40, or two threads may be included to provide flexibility in installation. The other end of passage fitting 40 defines a neck 48 having an outer diameter smaller than the remainder of passage fitting 40. A shoulder 50 at the inside extent of the thread 46 abuts the outer shell 22 of the diaphragm tank. A concave annular groove 52 in the holder 44 retains o-ring 42 in groove 34. To promote a watertight seal, the depth of groove 34 is less than the thickness of the o-ring 42.

To install the connector in the wall of a diaphragm tank, the neck 48 of passage fitting 40 is first inserted through the hole defined by the outer shell 22, gasket 28 and liner 30. O-ring 42 and holder 44 are sequentially mounted on neck 48. Neck 48 is then bent around holder 44. The bent neck 48 presses against the holder 44 to firmly retain the holder in place. The shell 22, gasket 28 and liner 30 are tightly clamped between shoulder 50 of passage fitting 40 and holder 44. In addition, because the depth of the groove 34 is less than the thickness of the o-ring 42, the o-ring 42 will be deformed to expand against the outside of passage fitting 40 as it is squeezed between the holder 44 and the liner 30, providing a watertight seal. This forms a watertight seal at the junction of the liner 30 and passage fitting 40. In addition, liner 30 will be squeezed by the holder 44 to fully engage gasket 28, preventing leakage around the gasket 28.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A diaphragm tank, comprising:
   an outer shell;
   a flexible diaphragm;
   a liner sealingly connected to the flexible diaphragm to define a bladder, the liner including an orifice and a raised portion surrounding the orifice defining a relief surface and having a first side surface bounding the orifice and a second side surface opposing the first side surface, wherein the relief surface extends the entire length of the raised portion;
   a passage fitting having an inner wall and a concentric, outer wall, with the passage fitting providing fluidic communication through the inner wall between an exterior of the outer shell and the bladder, with the passage fitting having a neck extending away from the inner wall and outwardly of the outer wall;
   an o-ring disposed on the relief surface;
   an annular holder mounted on the passage fitting, with the annular holder having a first leg and a second leg, wherein the first leg and the second leg are interconnected and have substantially L-shaped cross sections, the annular holder disposed about the o-ring and the second side surface to retain the o-ring on the relief surface adjacent to the orifice; and
   a gasket disposed between the liner and the outer shell;
   wherein a portion of the neck is bent to retain the annular holder against the o-ring, wherein the o-ring is abutted by the outer wall of the passage fitting, by the relief surface of the raised portion and by the first leg and the second leg of the annular holder and thereby fully enclosing the o-ring and preventing fluidic communication between a space between the liner and the outer shell and the bladder along the outer wall of the passage fitting.

2. The diaphragm tank of claim 1, wherein the passage fitting is disposed partially inside the outer shell and partially outside the outer shell and comprises a shoulder restricting motion of the passage fitting into the diaphragm tank.

3. A liner for use with a diaphragm tank and a through-wall connector, the through-wall connector comprising a passage fitting having an inner wall and a concentric, outer wall, with the passage fitting having a neck and adapted to extend into the diaphragm tank, an o-ring adapted to be mounted on the passage fitting, and an annular holder mounted on the passage fitting, with the annular holder having a first leg and a second leg, wherein the first leg and the second leg are interconnected and have substantially L-shaped cross sections, wherein:

the liner has a raised portion having a relief surface on which the o-ring is disposed, wherein the relief surface extends the length of the raised portion, the raised portion having a first side surface defining an orifice in the liner and a second side surface opposing the first side surface, wherein the o-ring is abutted by the outer wall of the passage fitting, but the relief surface of the raised portion and by the first leg and the second leg of the annular holder and thereby fully enclosing the o-ring, and, when the neck is bent over the annular holder, the annular holder is disposed about the o-ring and the second side surface, thereby retaining the o-ring on the relief surface adjacent to the orifice to prevent fluidic communication from an exterior side of the liner to an interior side of the liner along the outer wall of the passage fitting.

* * * * *